United States Patent
Roosloot et al.

(10) Patent No.: US 10,150,942 B2
(45) Date of Patent: Dec. 11, 2018

(54) CONTROL OF PH AND DISSOLVED GAS IN MEDIUM (71) Applicant: XPAND BIOTECHNOLOGY B.V., Bilthoven (NL)

(72) Inventors: Emerentius Gerardus Roosloot, Bilthoven (NL); Pieter Theo Elias Van Santen, Bilthoven (NL)

(73) Assignee: XPAND BIOTECHNOLOGY B.V., Bilthoven (NL)

( * ) Notice: Subject to any disclaimer, the term of this patent is extended or adjusted under 35 U.S.C. 154(b) by 204 days.

(21) Appl. No.: 14/903,580

(22) PCT Filed: Jul. 17, 2014

(86) PCT No.: PCT/NL2014/050488
§ 371 (c)(1),
(2) Date: Jan. 7, 2016

(87) PCT Pub. No.: WO2015/009151
PCT Pub. Date: Jan. 22, 2015

(65) Prior Publication Data
US 2016/0168528 A1   Jun. 16, 2016

(30) Foreign Application Priority Data

Jul. 17, 2013  (NL) ..................... 2011187

(51) Int. Cl.
*C12M 1/34* (2006.01)
*C12N 5/0775* (2010.01)
(Continued)

(52) U.S. Cl.
CPC ............ *C12M 41/26* (2013.01); *C12M 29/04* (2013.01); *C12M 29/06* (2013.01); *C12M 29/26* (2013.01);
(Continued)

(58) Field of Classification Search
CPC ...... C12M 29/04; C12M 29/06; C12M 29/26; C12M 41/26; C12M 41/34; C12N 5/0662;
(Continued)

(56) References Cited

U.S. PATENT DOCUMENTS 3,821,087 A * 6/1974 Knazek .................. C12M 25/10
435/297.4
4,999,298 A * 3/1991 Wolfe .................... C12M 25/10
435/293.1
(Continued)

FOREIGN PATENT DOCUMENTS

EP     2 130 905    12/2009
GB       26691      11/1914
(Continued)

OTHER PUBLICATIONS

International Search Report for PCT/NL2014/050488, dated Jun. 22, 2014, 4 pages.

*Primary Examiner* — Maureen Wallenhorst
(74) *Attorney, Agent, or Firm* — Morrison & Foerster LLP (57) ABSTRACT

A method and device to adjust the concentration of at least two gasses in a fluid, wherein the method involves adjusting the concentration of a first gas in the fluid by adjusting the concentration of a second gas in the fluid wherein the first and second gases are kept separate until dissolved in the fluid.

9 Claims, 7 Drawing Sheets (51) Int. Cl.
 *G01N 31/22* (2006.01)
 *C12M 1/00* (2006.01)

(52) U.S. Cl.
 CPC ........... *C12M 41/34* (2013.01); *C12N 5/0662* (2013.01); *G01N 31/221* (2013.01); *B01J 2219/00966* (2013.01); *Y10T 436/204998* (2015.01); *Y10T 436/209163* (2015.01); *Y10T 436/25875* (2015.01)

(58) Field of Classification Search
 CPC ......... Y10T 436/20; Y10T 436/204998; Y10T 436/207497; Y10T 436/209163; Y10T 436/255; Y10T 436/25875; G01N 31/221; B01J 2219/00966
 USPC ......... 436/68, 127, 133, 136, 138, 163, 178, 436/181; 422/83, 88; 435/4, 29, 30, 325, 435/326, 366, 383, 303.1
 See application file for complete search history.

(56) References Cited

U.S. PATENT DOCUMENTS

| | | | |
|---|---|---|---|
| 5,002,890 A * | 3/1991 | Morrison | C12M 23/06 210/396 |
| 5,888,807 A * | 3/1999 | Palsson | C07K 14/535 435/289.1 |
| 2004/0057869 A1* | 3/2004 | Dingley | A61M 1/1698 422/48 |
| 2005/0133104 A1 | 6/2005 | Plummer | |
| 2006/0019385 A1 | 1/2006 | Smith et al. | |
| 2011/0129389 A1* | 6/2011 | Brady | A61M 1/1698 422/48 |

FOREIGN PATENT DOCUMENTS

| | | |
|---|---|---|
| JP | 7-246086 | 9/1995 |
| WO | WO-2004/027016 | 4/2004 |
| WO | WO-2009/016078 | 2/2009 |

\* cited by examiner

CONTROL OF PH AND DISSOLVED GAS IN MEDIUM

CROSS-REFERENCE TO RELATED APPLICATIONS

This application is the national phase of PCT application PCT/NL2014/050488 having an international filing date of 17 Jul. 2014, which claims benefit of Dutch patent application No. 2011187 filed 17 Jul. 2013. The contents of the above patent applications are incorporated by reference herein in their entirety.

The present invention relates to a method to adjust the gas concentration of at least two gasses in a fluid. and to devices for adjusting the concentration of at least two gasses in a fluid. In particular the invention is directed to adjusting the concentration of oxygen and pH in cell culture medium, particularly in culturing of human cell, especially human stem cells.

BACKGROUND

Cells are usually cultured in a bioreactor where the conditions may be controlled. Bioreactors may be a closed system so as to avoid contamination from the outside world. This is especially true for mammalian cells, and in particular for human cells. Control of nutrients, oxygen, temperature and pH are of vital importance for culturing cells.

In common used bioreactors there is both a liquid phase and a gas phase. The control of e.g. dissolved oxygen in the medium occurs at the interphase of the gas phase and liquid phase. Carbon dioxide may be used to control the pH. Some bioreactors have only a liquid phase, see e.g. WO2011/142667 and a device is needed to control dissolved oxygen and the pH. Transfer of gasses such as oxygen to a fluid medium may be performed over a membrane. Common oxygenators comprise of a chamber comprising oxygen where medium is flown through. EP0343357 discloses an oxygenator using 0.132 inch inner diameter (ID) and 0.183 inch outer diameter (OD) silicon tube where the fluid is flown through. Air is pumped by an air pump into the shell side of the oxygenator. Due to the gas permeable properties of silicone, oxygen is transferred to the fluid. The pH can be controlled by controlling the dissolved carbon dioxide in the medium. U.S. Pat. No. 4,493,692 discloses a blood gas concentration control apparatus for regulating oxygen an carbon dioxide in extracorporeal blood. It discloses an oxygenator wherein a source of oxygen (100% $O_2$) and a source of carbon dioxide (95% $O_2$ and 5% $CO_2$) is connected. Both gasses are applied to the same oxygenator. WO2011/066481 discloses an extracorporeal membrane oxygenating control wherein an oxygen supply and carbon dioxide supply provide oxygen and carbon dioxide to the same membrane oxygenator.

The present inventors found that mixtures of oxygen and carbon dioxide and nitrogen, such as used in the prior art, give large fluctuations in the control of the pH and dissolved oxygen in a fluid. With a mixture of gasses, the pH could only be controlled within 0.5 pH units of the setpoint. Similarly, the control of the setpoint of the dissolved oxygen was in the range of 25% air saturation. For the culturing of mammalian cell, especially human cell and in particular human stem cells, these kind of controls are not tight enough to create a proper environment for the cells in a single phase bioreactor. In addition to the large variation of both the pH and dissolved oxygen around the setpoint, the control system for pH and dissolved oxygen was very slow.

SUMMARY OF THE INVENTION

Surprisingly it was found that when adjusting the concentration of dissolved oxygen and/or the adjusting of the pH by adjusting the concentration of dissolved carbon dioxide, was separated in place, the environment for the cultured cells can be controlled much better with smaller off-set variations.

Therefore, in a first aspect the present invention is directed to a method to adjust the concentration of at least two gasses in a fluid, comprising
  a) adjusting the concentration of a first gas in the fluid by a means for adjusting a first gas concentration, and
  b) adjusting the concentration of a second gas in the fluid by a means for adjusting a second gas concentration,
    wherein the means for adjusting the concentration of the first gas and the means for adjusting the concentration of the second gas are separate from each other.

In a second aspect the present invention is directed to a device to adjust the concentration of at least two gasses in a fluid comprising
  a) a means for adjusting a first gas concentration in a fluid, and
  b) a means for adjusting a second gas concentration in a fluid,
    wherein the means for adjusting the concentration of the first gas and the means for adjusting the concentration of the second gas are separate from each other.

The gasses are delivered to the fluid separately in the device and method. Thus before entering the fluid the first and second gas are not in contact with each other. Not until the first and second gas enter the fluid and are dissolved therein, the first and second gas may come in contact with each other. The mixing of the first and second gas thus takes place in the fluid. There is thus no mixing or contact of the first and second gas before the transfer to the fluid. There is thus only mixing or contact of the first and second gas after transfer to the fluid. There is thus no mixing or contact of the first and second gas while in the gas phase. There is thus only mixing or contact of the first and second gas after the first and second gas have dissolved into the fluid. In a preferred embodiment according to aspects and/or embodiments of the invention the first gas and the second gas are different.

In a preferred embodiment according to aspects and/or embodiments of the invention the first and second gas are separate while in the gas phase. In a preferred embodiment according to aspects and/or embodiments of the invention the first and second gas are separate until transferred into the fluid. In a preferred embodiment according to aspects and/or embodiments of the invention until dissolved in the fluid.

In a preferred embodiment according to aspects and/or embodiments of the invention the adjustment of the concentration of the first gas and/or the second gas may be performed by a mixtures of gasses.

In a preferred embodiment according to aspects and/or embodiments of the invention the first gas is oxygen. In a preferred embodiment according to aspects and/or embodiments of the invention the second gas is carbon dioxide.

In a preferred embodiment according to aspects and/or embodiments of the invention carbon dioxide is used for adjusting the pH.

In a preferred embodiment according to aspects and/or embodiments of the invention the dissolved oxygen in the fluid and/or pH of the fluid is monitored.

In a preferred embodiment according to aspects and/or embodiments of the invention the means for adjusting the concentration of the first gas comprises a first gas chamber wherein the first gas or a mixture of gasses comprising the first gas is present, comprising a first membrane separating the fluid from the first gas, wherein the membrane is made of a gas permeable material. In a preferred embodiment according to aspects and/or embodiments of the invention the means for adjusting the concentration of the second gas comprises a second gas chamber wherein the second gas or a mixture of gasses comprising the second gas is present, comprising a second membrane separating the fluid from the second gas, wherein the second membrane is made of a gas permeable material. In a preferred embodiment according to aspects and/or embodiments of the invention the means of adjusting concentration of the first gas and means of adjusting concentration of the second gas are separate devices, or are in one device wherein the first and second gas chamber are separated.

In a preferred embodiment according to aspects and/or embodiments of the invention the gas permeable material is selected from the group consisting of silicone, silicone rubber, ethyl cellulose derivative, polytetrafluoroethylene, polyethylene, polypropylene, hydrophobic polypropylene, dimethylsiloxane, polymethylpentene.

DETAILED DESCRIPTION

Figures

In a second aspect the invention relates to a device to adjust the concentration of at least two gasses.

The gasses are delivered to the fluid separately in the device and method. Thus before entering the fluid the first and second gas are not in contact with each other. Not until the first and second gas enter the fluid and are dissolved therein, the first and second gas may come in contact with each other. The mixing of the first and second gas thus takes place in the fluid. There is thus no mixing or contact of the first and second gas before the transfer to the fluid. There is thus only mixing or contact of the first and second gas after transfer to the fluid. There is thus no mixing or contact of the first and second gas while in the gas phase. There is thus only mixing or contact of the first and second gas after the first and second gas have dissolved into the fluid.

The present method and device are very suitable for cell culture in fluid, especially for closed systems with the fluid as the single phase. For the purpose of the present invention a fluid is a liquid that is deformable under appliance of stress. Preferably a fluid according to the present invention has a bostwick value at room temperature of at least 0.1, more preferably at least 0.5, more preferably at least 1, more preferably at least 2, more preferably at least 4, more preferably at least 6, and most preferably at least 9. The bostwick value is expressed as centimeter per second (cm/s) and is the distant a liquid or fluid flows at a certain temperature for a certain time. A typical Bostwick measurement protocol uses a Bostwick equipment consisting of a 125 ml reservoir provided with a outlet near the bottom of a horizontally placed rectangular tub and closed with a vertical barrier. The tub's bottom is provided with a 25 cm measuring scale, extending from the outlet of the reservoir. When equipment and sample both have a desired temperature (e.g. room temperature or 15° C., the reservoir is filled with 125 ml of the sample after it has been shaken by hand ten times up and down. When the closure of the reservoir is removed the sample flows from the reservoir and spreads over the tub bottom. The path length of the flow is measured after 15 seconds. The value, expressed as cm per seconds is the Bostwick value, which is used as yard stick for pourability.

The fluidity of a liquid may also be expressed by viscosity. In a preferred embodiment of the method or device of the present invention and/or embodiments thereof the viscosity of the fluid at room temperature is less than 250 Pa·s, more preferably less than 150 Pa·s, more preferably less than 100 Pa·s, more preferably less than 50 Pa·s, and more preferably less than 30 Pa. In a preferred embodiment of the method or device of the present invention and/or embodiments thereof the viscosity of the fluid at room temperature is between 0.01 and 10 mPa·s, more preferably between 0.1 and 5 mPas, more preferably between 0.2 and 1 mPa·s, more preferably between 0.3 and 0.8 mPa·s, and more preferably between 0.4 and 0.7 mPa·s, more preferably between 0.5 and 0.6 mPa·s.

For the purpose of he present invention percentages (%) for gasses are vol % unless otherwise indicated.

In a preferred embodiment of the method and device of the present invention and/or embodiments thereof, the fluid is a liquid culture medium and may be any kind of fluid that may be used for culturing cells. Cell culturing with fluid has the advantage that medium may be refreshed and that thus the cells may grow longer. Non limiting examples of fluid are basal medium eagle (BME), dulbecco's modified eagle medium (DMEM), minimum essential medium (MEM), minimum essential media alpha (NEMA), Glasgow modified minimum essential medium (GMEM), Iscove's modified Dulbecco's medium (IMDM), Leibovits L15 medium, McCoy's 5A medium, F10 nutrient mix, F12 nutrient mix, MCDB 153, media 199, RPMI 1640 medium, Waymouth's MB 752/1 medium, Schneider's Drosophila medium, Grace's insect medium, and Bioinsect-1 serum free medium. Depending on the cells to be cultured, the fluid may comprise additional ingredients such as ingredients selected from the group comprising fetal bovine serum (FBS), platelet lysate (PL), growth factors, antibiotic such as penicillin or streptomycin, ascorbic acid-2-phosphate (asap), peptides and/or aminoacids, e.g. Glutamax, dexamethasone growth factors such as e.g. basic fibroblast growth factor human recombinant and EGF, carbohydrates such as D (+) glucose, sodium hypoxanthine, aminopterin, thymidine, lipids, saturated and unsaturated fatty acids, PUFA, vitamins, phospholipids, minerals, human transferrin, human insulin, progesterone, putrescine, selenite, surfactants such as non-ionic surfactants, antioxidants, 2-mercaptoethanol, cholesterol, hormones, and hydrocortisone.

The cells to be cultured may be any kind of cells, such as bacterial cells, fungi, yeast cells, plant cells, algae, insect cells, mammalian cells. In a preferred embodiment of the invention and/or embodiments thereof the cells are mammalian cells, more preferably human cells, more preferably progenitor cells, more preferably stem cells, however the cells may also be chosen from embryonic cells, skin cells, kidney cells, pancreas cells, liver cells, red blood cells, white blood cells, bone cells, cartilage cells, muscle cells, lung cells, eye cells, ovary cells, omnipotent cells, pluripotent cells, cancer cells. The cells may be primary cells but may also be from a cell-line. The cells may be adherent cells or non-adherent cells. The cells may be primary cells.

The present invention is directed to adjusting the concentration of two or more gasses in a fluid. Most used gasses are air, oxygen ($O_2$), carbon dioxide ($CO_2$), nitrogen ($N_2$) helium, and other inert gasses. The prior art shows that if the concentration of two or more gasses are to be adjusted, this is done via one oxygenator, or one gas exchange means. Sources of the two or more gasses provide the gas in the same space. However, the present inventors found that when the concentration of two or more gasses is to be adjusted and this is done in the prior art way, the accuracy of the adjustment is not great. In cultures with 'sensitive' cells, such as e.g. human stem cells, this is not enough. It was surprisingly found that when the step of adjusting the concentration of a first gas in the fluid by a means for adjusting a first gas concentration and the step of adjusting the concentration of a second gas in the fluid by a means for adjusting a second gas concentration is performed separated from each. This means that there is a separate means for the adjusting of the concentration of the first gas and a separate means for adjusting the concentration of the second gas. It is to be understood that mixing of the first and second gas does not take place in the gas chamber. The mixing of the first and second gas occurs only after the transfer over a membrane to the fluid, when the first and second gas are dissolved. The first and second gas are thus separate when in the gas phase, meaning that while in the gas phase the first and second gas do not come in contact with each other. In a preferred embodiment of the method or device of the invention and/or embodiments thereof the concentration adjustment means may be each a separate device, or may be placed in one device. If the two or more concentration adjustment means are in one device then this device is designed in such a way that the two or more gasses do not come in contact with each other, e.g. by placing a wall between each concentration adjustment means, or by placing the concentration adjustment means next to each other without having contact between the at least two gasses. In a preferred embodiment of the method or device of the invention and/or embodiments thereof, the adjusting of the concentration of the first gas and the adjusting of the concentration of the second gas are performed simultaneously. The first and second gas are transferred to the fluid separately. After transfer of the first and second gas over a membrane to the fluid, these gases may be mixed in the fluid. There is thus no contact between the first and second gas in the device, or when in the adjustments means. There is thus no mixing of the first and second gas prior to the transfer over the membrane. It was found that using one device for adjusting the concentration of at least two gasses where the first and second gas are in contact with each other have a large offset, see e.g. FIGS. 3 and 4. It was also found, that using a single adjusting device for adjusting the concentration of the at least two gasses but then using the single adjusting device separately for the first gas and separately for the second gas, i.e. consecutively, and not simultaneously, like "time-sharing" also does not give good results.

In a preferred embodiment of the method or device of the invention and/or embodiments thereof more than two gasses are used. It is to be understood that each additional gas requires a separate concentration adjustment means. Thus if the concentrations of 3 gasses are to be adjusted, three separate means for adjusting the concentration for each gas are required. In a preferred embodiment of the invention of the method or device and/or embodiments thereof the first gas and the second gas are different. In a preferred embodiment of the invention of the method or device and/or embodiments thereof the adjustment of the concentration of the first gas and/or second gas may be performed by a mixture of gasses. In a preferred embodiment of the invention of the method or device and/or embodiments thereof the means for adjusting the concentration of the first and/or the means for adjusting the concentration of the second gas comprise a mixtures of gasses. In a preferred embodiment of the invention of the method of device and/or embodiments thereof, gasses the mixture of gasses to adjust the concentration of the first gas does not comprise the second gas, and the mixture of gasses to adjust the concentration of the second gas does not comprise the first gas. As shown in the experiments when using one device or means for a adjusting two or more gasses, the gasses are simultaneously present and the adjustment of the concentration is performed at the same time but also at the same position. Without wishing to be bound to theory, it is believed that the simultaneous adjustment of the concentration of more than 1 gas at the same position, gives the large variations in offset of the values of the dissolved gasses. It was also seen that a mixture of gasses may work very well. The concentration of the gas to be adjusted in the gas mixture depends on many factors, such as the concentration of the gas that is to be reached, the means of adjusting the concentration of the gas, such as the volume of the gas or mixture of gasses to be used, the partial pressure of the gas to be adjusted, the transfer rate of the gas to be adjusted to the fluid, the means of transfer of the gas to the fluid. In particular in case a membrane is used to transfer gas to the fluid, the concentration of the gas to be adjusted in the mixture of gasses, depends on the type of membrane, and the surface of the membrane. Furthermore, the concentration of the gas to be adjusted in the gas mixture depends on the volume of fluid used to perform the adjustment of the concentration of the gas. In general, the adjustment of the concentration of the gas in the fluid is performed on a part of the fluid. The means of adjusting the concentration of the gas in the present invention, is positioned on a part of the fluid. The volume of fluid where the adjustment of the concentration of the gas takes place is important for the part of the gas to be adjusted when a mixture of gasses is used to adjust the concentration. For example if a large volume is used for adjusting the concentration of the gas, then the part of the gas to be adjusted in the mixture comprising the gas to be adjusted may be lower than when the volume is lower. Similar, if the partial pressure of the gas to be adjusted is high a lower volume may suffice, or a lower concentration of the gas to be adjusted in the mixture of gasses is needed. Also if the transfer rate of the gas to be adjusted is high, a lower volume, or a lower concentration of the gas to be adjusted in the mixture of gasses is needed It also depends on how much the concentration needs to be adjusted. If a high concentration of the gas is needed, then a larger volume of the gas, or a higher concentration f the gas to be adjusted in a mixture of gasses may be used. It was also seen that when a mixture of gasses was used, sometimes the present of the other gas was permitted. For example in a mixture of gasses to adjust the concentration of a first gas, the second gas may be present, however in a concentration of less than 20 vol %, more preferably less than 15 vol %, more preferably less than 10 vol %, more preferably less than 8 vol %, more preferably less than 5 vol %, more preferably less than 3 vol %, more preferably less than 2 vol %, and more preferably less than 1 vol %. Also in a mixture of gasses to adjust the concentration of a second gas, the first gas may be present, however in a concentration of less than 20 vol %, more preferably less than 15 vol %, more preferably less than 10 vol %, more preferably less than 8 vol %, more preferably less than 5 vol %, more preferably less than 3 vol %, more preferably less than 2 vol %, and more preferably less than 1 vol %. Whether in a mixture of gasses the other gas may be present or not and to what extend also depends on the very same factors described above, such as depending on the partial pressure of the first and second gas, the transfer rate of the first and second gas, the volume of the gas or mixture of gasses for the concentration adjustment, the required concentration of the gas to be adjusted in the fluid etc. A skilled person may easily adjust the mixture of gasses to his needs. Partial pressure of gasses and transfer rate of gasses are known for gasses and so a skilled person is well equipped to calculate for example the volume needed to adjust the concentration of a given gas to be adjusted, or is well able to determine the minimal part of the gas to be adjusted in a mixture of gasses. In a preferred embodiment of the invention and/or embodiments thereof the concentration of first gas and/or the second gas is adjusted by a mixture of gasses. Suitable gasses are oxygen ($O_2$), carbon dioxide ($CO_2$), nitrogen ($N_2$) Air and helium (He). Suitable mixtures of gasses are air, oxygen ($O_2$) with nitrogen ($N_2$), oxygen with air, carbon dioxide with air, oxygen with helium (He), air with nitrogen, carbon dioxide with nitrogen, or carbon dioxide with helium. In a preferred embodiment of the invention and/or embodiments thereof the first gas is oxygen. In a preferred embodiment of the method and/or device the present invention and/or embodiments thereof the mixture of gasses to adjust the concentration of oxygen comprises 1-99 vol % oxygen, more preferably from 2-95 vol % oxygen, more preferably from 5-90 vol % of oxygen, more preferably from 7-88 vol % oxygen, more preferably from 10-85 vol % of oxygen, more preferably from 15-83 vol % of oxygen and even more preferably from 20-80 vol % of oxygen, or even from 25-75 vol % of oxygen, more preferably from 30-70 vol % of oxygen, more preferably from 35-65 vol % of oxygen, more preferably from 40-60 vol % of oxygen, more preferably from 45-55 vol % of oxygen and even about 50 vol % of oxygen. In a preferred embodiment the gas mixture with oxygen comprises nitrogen, air, and/or helium. Suitable mixtures of oxygen are 50 vol % oxygen with 50 vol % air, or 20 vol % of oxygen with 80 vol % of nitrogen, or 20 vol % of oxygen with 80% of air, or 80% air with 20% of nitrogen. It is to be understood that as a source of oxygen, pure oxygen may be used, but also air which comprises about 20 vol % of oxygen. In a preferred embodiment of the method and/or device the present invention and/or embodiments thereof, the mixture comprising oxygen preferably comprises less than 20 vol % of the second gas, more preferably less than 15 vol %, more preferably less than 10 vol %, more preferably less than 8 vol %, more preferably less than 5 vol %, more preferably less than 3 vol %, more preferably less than 2 vol %, and more preferably less than 1 vol % of the second gas. In a preferred embodiment of the method or device of the invention and/or embodiments thereof the second gas is carbon dioxide. The carbon dioxide mixture may comprise 1-99 vol % carbon dioxide, more preferably from 2-95 vol % carbon dioxide, more preferably from 5-90 vol % of carbon dioxide, more preferably from 7-88 vol % carbon dioxide, more preferably from 10-85 vol % of carbon dioxide, more preferably from 15-83 vol % of carbon dioxide and even more preferably from 20-80 vol % of carbon dioxide, or even from 25-75 vol % of carbon dioxide, more preferably from 30-70 vol % of carbon dioxide, more preferably from 35-65 vol % of carbon dioxide, more preferably from 40-60 vol % of carbon dioxide, more preferably from 45-55 vol % of carbon dioxide and even about 50 vol % of carbon dioxide. In a preferred embodiment the gas mixture to adjust the concentration of carbon dioxide comprises nitrogen, air, or helium. Suitable mixtures with carbon dioxide are 50 vol % carbon dioxide and 50 vol % air, or 50 vol % of carbon dioxide with 50 vol % of nitrogen. In a preferred embodiment of the method and/or device the present invention and/or embodiments thereof, the mixture comprising carbon dioxide preferably comprises less than 20 vol % of the first gas, more preferably less than 15 vol %, more preferably less than 10 vol %, more preferably less than 8 vol %, more preferably less than 5 vol %, more preferably less than 3 vol %, more preferably less than 2 vol %, and more preferably less than 1 vol % of the first gas. In a preferred embodiment of the invention and/or embodiments thereof the concentration of carbon dioxide in the fluid is used for adjusting the pH. It depends on the fluid and the purpose of the dissolved gas how much of the gas is used. A skilled person will be able to find a suitable gas amount. For example for culture media, it depends on the medium, the cells to be cultured, and the gas to be dissolved. In a preferred embodiment of the method or device of the invention and/or embodiments thereof the concentration of the gasses is measured. In a more preferred embodiment the concentration of the gasses is monitored and a feed-back is provided such that the adjusting of the concentration of the gasses is automatically controlled. In a preferred embodiment oxygen in the fluid and/or pH of the fluid is monitored. In a preferred embodiment of the method and/or device the present invention and/or embodiments thereof, the concentration of the gasses to be adjusted is measured after the concentration of each of the gasses is adjusted. In a suitable embodiment, the means for measuring the concentration of the gasses to be adjusted is placed after the means for adjusting the concentration of the gasses. In a preferred embodiment of the method and/or device the present invention and/or embodiments thereof, the concentration of the gasses to be adjusted is measured before the concentration of each of the gasses is adjusted, so to be able to determine the requirements of the adjustment of the concentration of the gasses. In a preferred embodiment of the method and/or device the present invention and/or embodiments thereof, the concentration of the gasses to be adjusted is measured before and after the concentration of each of the gasses is adjusted.

In a preferred embodiment of the method or device of the invention and/or embodiments thereof the means for adjusting the concentration of first gas comprises a first gas chamber wherein the first gas is present comprising a first membrane separating the gas from the fluid, and the membrane is made of a gas permeable material. In a preferred embodiment of the invention and/or embodiments thereof the means for adjusting the concentration of the second gas comprises a second gas chamber wherein the second gas is present comprising a second membrane separating the gas from the fluid, the second membrane is made of a gas permeable material. In a preferred embodiment the first and second gas are not mixed in the gas chamber.

In a preferred embodiment of the method and/or device the present invention and/or embodiments thereof, the gas chamber in the means for adjusting the concentration of the gas, comprises a mixture of gasses comprising the gas to be adjusted. For example, the first gas chamber in the first means for adjusting the concentration of the first gas, comprises a mixture of gasses comprising the first gas. In another example, the second gas chamber in the second means for adjusting the concentration of the second gas, comprises a mixture of gasses comprising the second gas. In a suitable means of adjusting the concentration of gas in a fluid according to the invention and/or embodiments thereof the membrane is a tube that runs through a chamber wherein gas may be held. The fluid suitably flows through the inner space of the membrane tube, and the gas is present on the outside of the membrane tube. The gas diffuses through the gas permeable material of the membrane thereby influences the concentration of the dissolved gasses in the fluid. If the partial pressure of a gas on the side of the membrane comprising the gas, is higher than the partial pressure of the gas on the side of the membrane comprising the fluid, then the gas will diffuse from the gas-side to the fluid-side of the membrane and the concentration of the dissolved gas in the fluid will increase. If the partial pressure of a gas on the fluid side of the membrane, i.e. the side with where fluid flows, is higher then the gas will diffuse from the fluid-side to the gas-side of the membrane and the concentration of the dissolved gas in the fluid will decrease. In certain suitable embodiments of the present invention and/or embodiments thereof, an enclosed volume wherein the fluid flows, wherein at least a part of the surface of the enclosed volume comprises a membrane, the enclosed volume comprising the fluid runs through a chamber containing gas. The enclosed volume provides a volume for the fluid but prevents direct contact between the fluid and the gas. Preferably the enclosed volume is in a tubular form. Preferably the material of the enclosed volume consist entirely of a membrane. In a preferred embodiment the enclosed volume is a tube consisting of a gas permeable membrane. In a preferred embodiment, of the method and/or device of the invention and/or embodiments thereof the enclosed volume holding the fluid continues after leaving the gas chamber, and entering the gas chamber. In a preferred embodiment of the method and/or device of the present invention and/or embodiments thereof the volume of the gas chamber is between 0.5 and 1000 mL, more preferably between 1 and 500 mL, more preferably between 2 and 250 mL, more preferably between 3 and 100 mL, more preferably between 4 and 80 mL, and more preferably between 5 and 70 mL, more preferably between 6 and 50 mL, more preferably between 7 and 45 mL, more preferably between 8 and 40 mL, more preferably between 9 and 35 mL, more preferably between 10 and 30 mL, more preferably between 11 and 25 mL, more preferably between 12, and 20 mL, more preferably between 13 and 18 mL, and more preferably between 14 and 16 mL. It is to be understood that it depends on the purpose of the dissolved gasses what the volume of the gas chamber should be. The volume of the gas chamber of the first concentration adjusting means and the volume of the gas chamber of the second concentration adjusting means may be different, depending on the gasses, the amount needs to be dissolved, the requirement of the system etc. A skilled person will be able to adjust the method or device to its needs. Suitably for a bioreactor of 50-1000 mL the gas chamber for oxygen is 10-60 mL, more preferably from 20-50 mL, more preferably from 25-45 mL, more preferably from 30-40 mL. Suitably for a bioreactor of 50-1000 mL the gas chamber for carbon dioxide is 0.5-10 mL, more preferably from 1-8 mL, more preferably from 2-6 mL, more preferably from 2.5 to 5 mL and more preferably from 3-4 mL. For cell culturing purposes the volume of fluid that is in contact with the gas chamber via the membrane is for a bioreactor of about 50-1000 mL for oxygen about 1-30 mL, more preferably from 2 to 25 mL, more preferably from 3 to 22 mL, more preferably from 5 to 20 mL, more preferably from 7 to 15 mL and more preferably from 10-12 mL. For cell culturing purposes the volume of fluid that is in contact with the gas chamber via the membrane is for a bioreactor of about 50-1000 mL for carbon dioxide about 0.05-5 mL, more preferably from 0.1 to 4.5 mL, more preferably from 0.2 to 4 mL, more preferably from 0.5 to 3 mL, more preferably from 0.7 to 2.5 mL and more preferably from 1-2 mL. Of course, the present invention and/or embodiments thereof may have different dimension depending on the purpose of the method or device, depending on the gasses used, depending on the requirement of the concentration of the gasses, etc. A skilled person is well able to adjust the volumes of the gas chamber and volume of fluid in contact with the gas chamber to the needs of the purpose of the method or device.

Suitable means of adjusting the concentration of a gas in fluid is an oxygenator. It is to be understood that an oxygenator may be used also for gasses other than oxygen, such as carbon dioxide, nitrogen and mixtures of gasses.

In a preferred embodiment of the method or device of the invention and/or embodiments thereof the concentration adjustment step of the first gas and the concentration adjustment step of the second gas may be consecutive. Suitably the concentration adjustment means of the at least two gasses are positioned adjacent, like beads on a string, or the concentration adjustment means are placed together in one device, having separate gas chambers.

In a preferred embodiment of the method or device of the invention and/or embodiments thereof the gas permeable material is selected from the group consisting of silicone, silicone rubber, ethyl cellulose derivative, polytetrafluoroethylene, polyethylene, polypropylene, hydrophobic polypropylene, dimethylsiloxane, polymethylpentene. The gas permeable material is a material that is permeable for gas but not for the fluid, it is a semi-permeable material.

EXAMPLES

Figure 1:
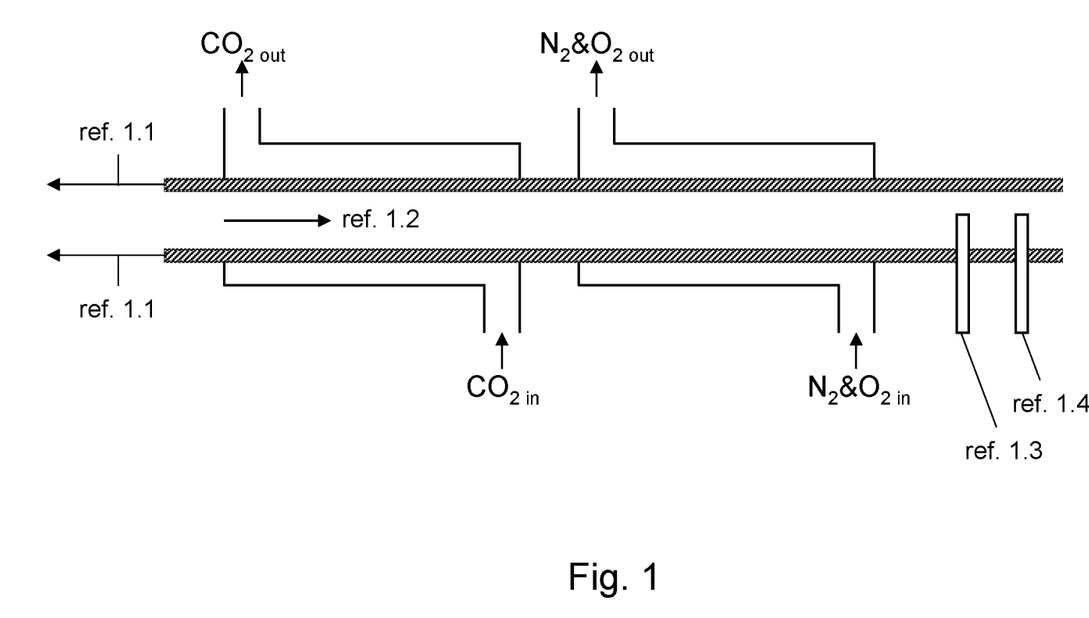
FIG. 1: Scheme of a device according to the invention with $CO_2$ as the first gas, and a mixture of $N_2$ and $O_2$ as the second gas.
Figure 2:
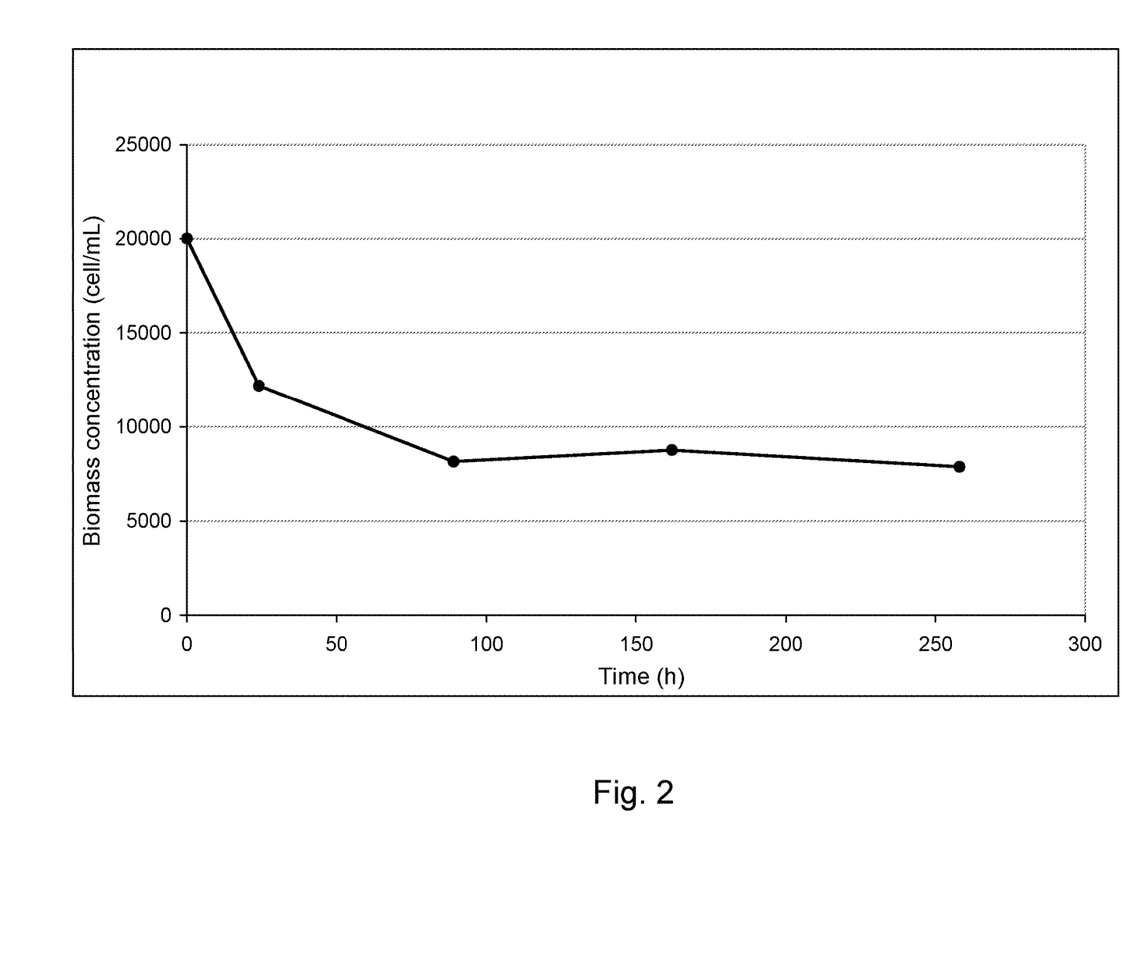
FIG. 2: Growth of cells in a bioreactor with a combined gas exchange
Figure 3:
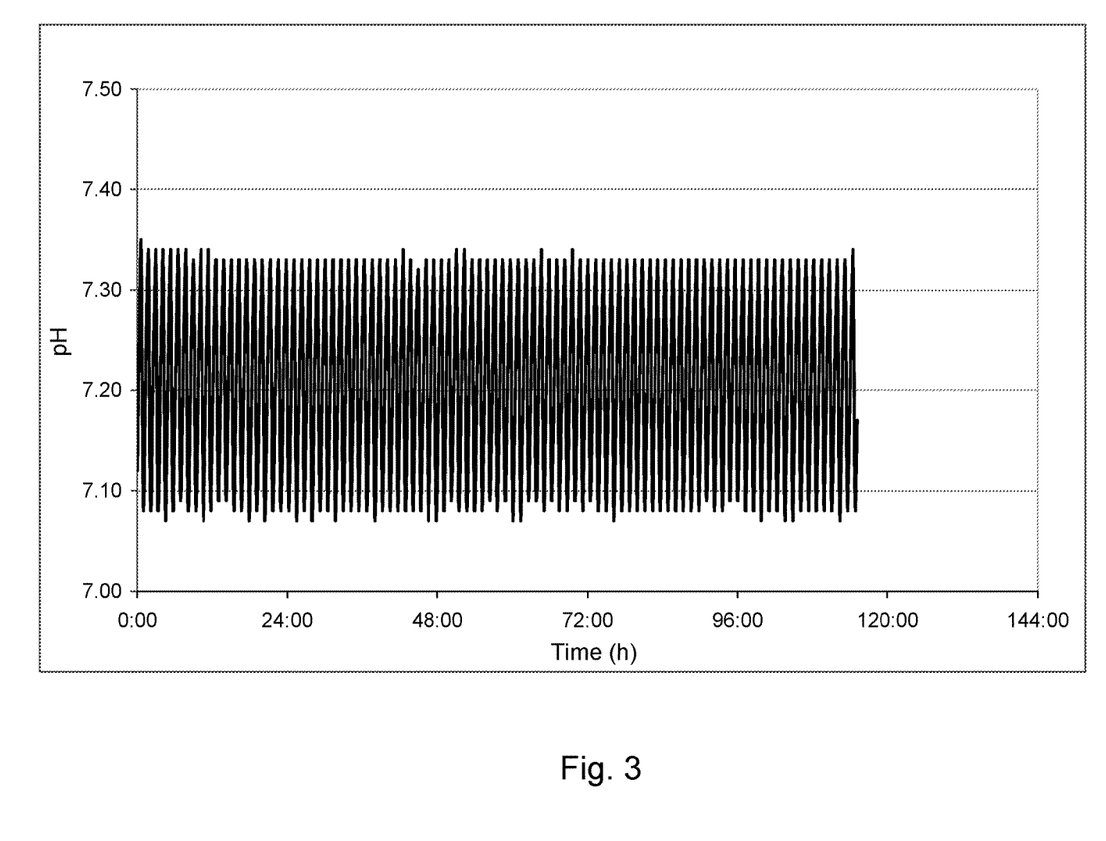
FIG. 3: Measured pH in a bioreactor with a combined gas exchange
Figure 4:
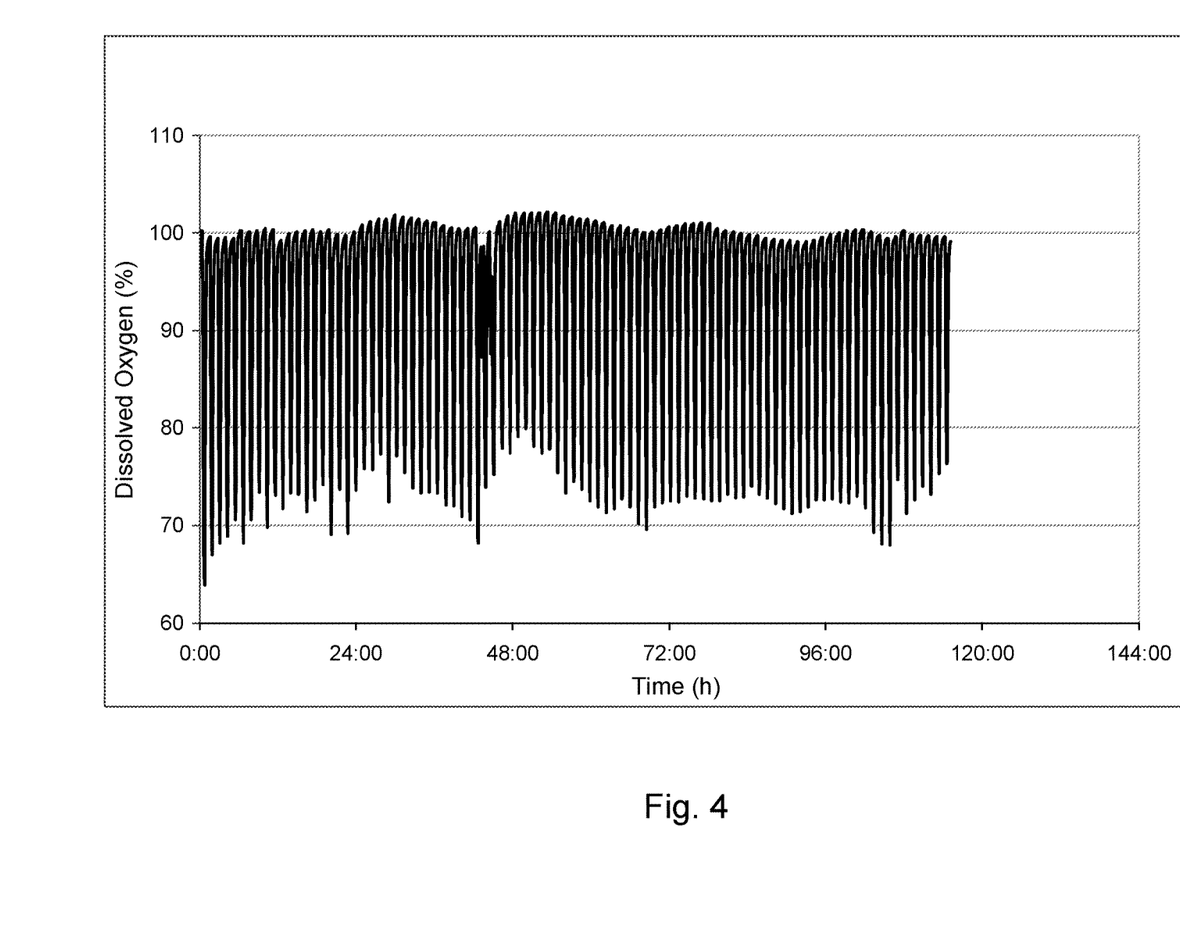
FIG. 4: Measured dissolved oxygen (DO) in a bioreactor with a combined gas exchange
Figure 5:
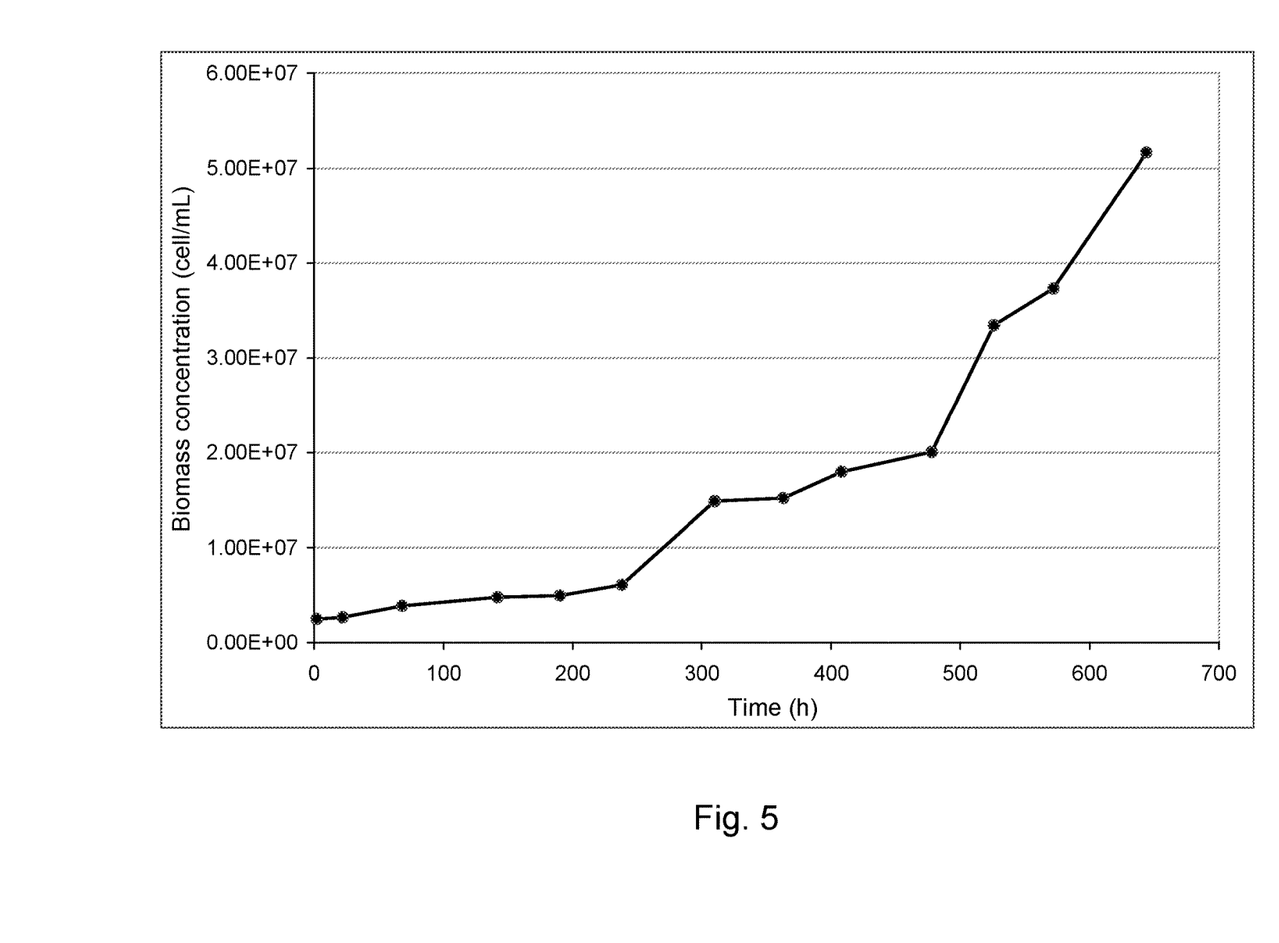
FIG. 5: Growth of cells in a bioreactor with a separate gas exchange module
Figure 6:
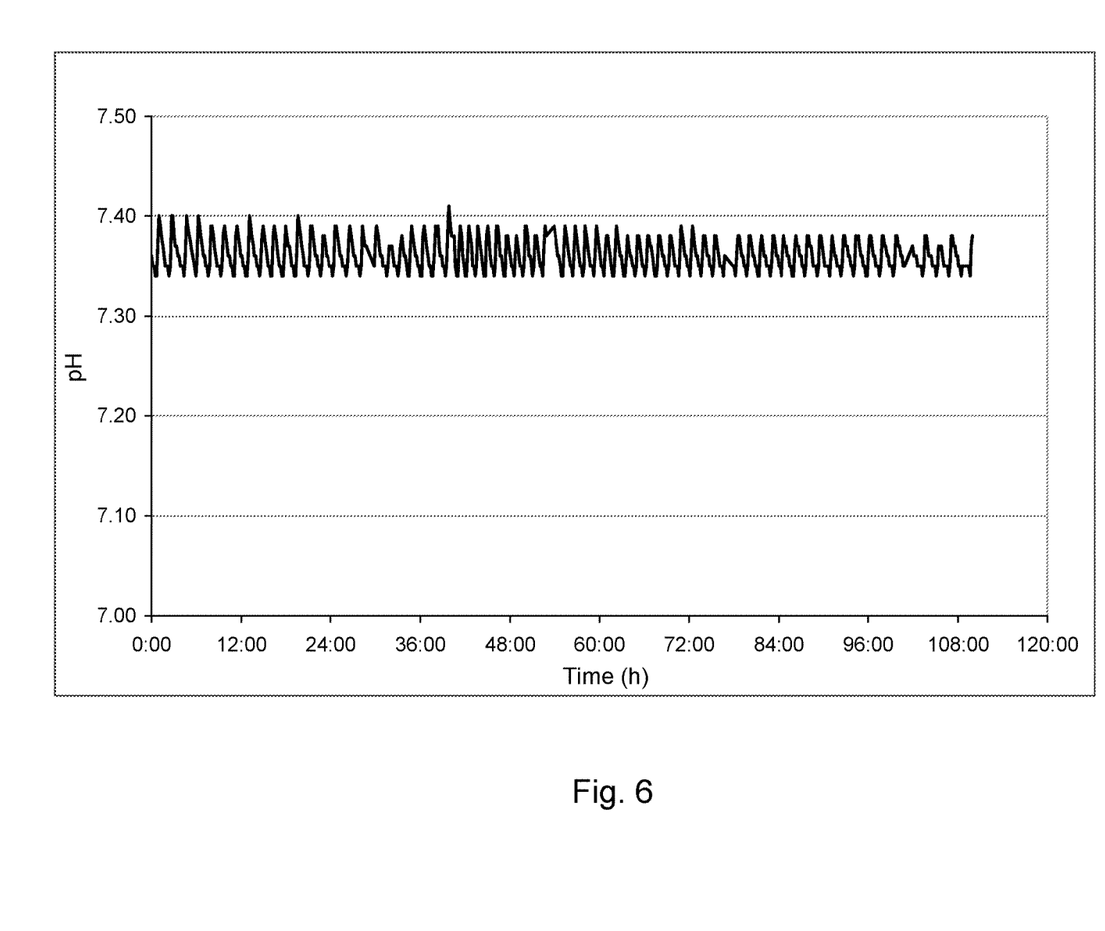
FIG. 6: Measured pH in a bioreactor with carbon dioxide and oxygen in separate gas exchange modules
Figure 7:
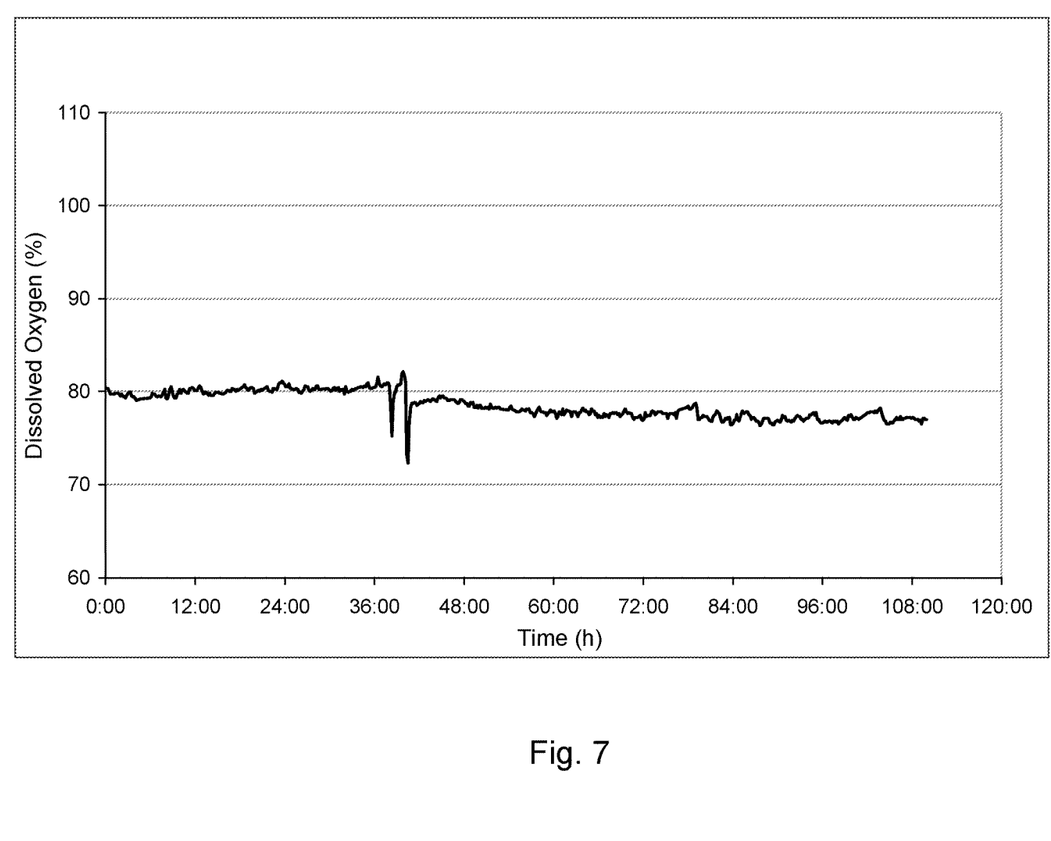
FIG. 7: Measured dissolved oxygen (DO) in a bioreactor with carbon dioxide and oxygen in separate gas exchange modules In a first aspect the invention relates to a method to adjust the concentration of at least two gasses, e.g. dissolved oxygen (DO) and carbon dioxide (pH) in a fluid.

Mesenchymal stem cells were cultured in a alpha-MEM liquid medium comprising microcarriers with a concentration of 20 $cm^2$/mL. The system was inoculated with $2.76*10^6$ cells from a donor in 135 mL. Cells were regularly monitored. Medium was refreshed at least every 3-4 days. Oxygen and pH controls were employed in a mixed gas-chamber by a gas flow of 95 vol % air with 5 vol % of carbon dioxide at 100 mL/min and the control was set at 40% dissolved oxygen and pH 7.3. Although the cells attached well to the microcarriers at first, no cell growth was observed (see FIG. 2). Oxygen and pH was measured as well and as can be seen in FIGS. 3 and 4, large variations of dissolved oxygen and pH was seen both in the inlet and outlet of bioreactor. Metabolites were measured as well and it was seen that the metabolites did not get depleted from the medium. In addition waste products such as lactate and ammonia did not reach inhibitory levels. The experiment was repeated with a change that the oxygen and pH were separately controlled having a separate gas chamber for oxygen and a separate gas chamber for carbon dioxide to control the pH, such as the one depicted in FIG. 1. As can be seen in FIG. 5 the cells grow well. As can be seen from FIGS. 6 and 7 the variation in dissolved oxygen and pH is much smaller with a system wherein oxygen and carbon dioxide are controlled separately.

The invention claimed is:

1. A method to adjust the concentration of $O_2$ and the pH of a fluid, comprising
   a) adjusting the concentration of $O_2$ in the fluid by controlling a flow of oxygen to the fluid, and
   b) adjusting the pH of the fluid by controlling a flow of $CO_2$ into the fluid,
   wherein the $O_2$ and $CO_2$ are kept separate until dissolved in the fluid, whereby they adjust the pH and $O_2$ concentration, and
   wherein the flow of $O_2$ is controlled by a first gas chamber wherein the $O_2$ is present, said chamber comprising a first membrane separating the fluid from the $O_2$, wherein the first membrane is made of a gas permeable material, wherein the flow of $CO_2$ is controlled by a second gas chamber wherein the $CO_2$ is present, said chamber comprising a second membrane separating the fluid from the $CO_2$, wherein the second membrane is made of a gas permeable material, and wherein the first and second gas chambers are separate from each other.

2. The method of claim 1 wherein the fluid is a liquid culture medium for culturing cells.

3. The method of claim 1 wherein the oxygen is supplied in admixture with nitrogen.

4. The method of claim 1 wherein the dissolved oxygen in the fluid and/or pH of the fluid is monitored.

5. The method of claim 1 wherein the chambers are separately contained in one device.

6. The method of claim 1 wherein the gas permeable material is selected from the group consisting of silicone, silicone rubber, ethyl cellulose derivative, polytetrafluoroethylene, polyethylene, polypropylene, hydrophobic polypropylene, dimethylsiloxane and polymethylpentene.

7. A device to supply a first gas and a second gas to a fluid in a fluid container, comprising
   a) a first chamber containing a first gas for effecting and for adjusting a flow of the first gas into said fluid container in said device, the first chamber comprising a first membrane for separating the fluid from the first gas, wherein the first membrane is made of a gas permeable material, and
   b) a second chamber containing a second gas for effecting and for adjusting a flow of the second gas into said fluid container in said device, the second chamber comprising a second membrane for separating the fluid from the second gas, wherein the second membrane is made of a gas permeable material,
   wherein the chambers for effecting and adjusting the flow of the first gas and for effecting and adjusting the flow of the second gas and are separate from each other.

8. The device of claim 7 wherein the fluid container is configured as a liquid culture medium for culturing cells.

9. The device of claim 7 wherein the gas permeable material is selected from the group consisting of silicone, silicone rubber, ethyl cellulose derivative, polytetrafluoroethylene, polyethylene, polypropylene, hydrophobic polypropylene, dimethylsiloxane and polymethylpentene.

* * * * *

UNITED STATES PATENT AND TRADEMARK OFFICE
CERTIFICATE OF CORRECTION

| | | |
|---|---|---|
| PATENT NO. | : 10,150,942 B2 | Page 1 of 1 |
| APPLICATION NO. | : 14/903580 | |
| DATED | : December 11, 2018 | |
| INVENTOR(S) | : Emerentius Gerardus Roosloot et al. | |

It is certified that error appears in the above-identified patent and that said Letters Patent is hereby corrected as shown below:

On the Title Page

Item (73), the Assignee name should be changed as follows:
"XPAND BIOTECHNOLOGY B.V.,
Bilthoven (NL)"
To:
-- SCINUS CELL EXPANSION B.V.,
Bilthoven (NL) --

Signed and Sealed this
Nineteenth Day of February, 2019

Andrei Iancu
*Director of the United States Patent and Trademark Office*